United States Patent [19]
Bales et al.

[11] Patent Number: 6,024,708
[45] Date of Patent: *Feb. 15, 2000

[54] RADIAL JAW BIOPSY FORCEPS

[75] Inventors: Thomas O. Bales, Coral Gables;
Charles R. Slater, Fort Lauderdale;
Kevin W. Smith, Miami, all of Fla.

[73] Assignee: Symbiosis Corporation, Miami, Fla.

[*] Notice: This patent is subject to a terminal disclaimer.

[21] Appl. No.: 08/928,453

[22] Filed: Sep. 12, 1997

Related U.S. Application Data

[63] Continuation of application No. 08/458,215, Jun. 2, 1995, Pat. No. 5,666,965, which is a continuation of application No. 07/837,046, Feb. 18, 1992, Pat. No. 5,507,296, which is a continuation of application No. 07/521,766, May 10, 1990, Pat. No. 5,133,727.

[51] Int. Cl.[7] .............................. A61B 17/28; A61B 10/00
[52] U.S. Cl. ............................................................. 600/564
[58] Field of Search .................................... 600/562–568; 606/167–171, 205–210

[56] References Cited

U.S. PATENT DOCUMENTS

| | | |
|---|---|---|
| 825,829 | 7/1906 | Heath . |
| 2,994,321 | 8/1961 | Tischler .................................. 600/564 |
| 3,895,636 | 7/1975 | Schmidt . |
| 3,921,640 | 11/1975 | Freeborn . |
| 4,200,111 | 4/1980 | Harris . |
| 4,427,014 | 1/1984 | Bel et al. ............................... 600/564 |
| 4,522,206 | 6/1985 | Whipple et al. . |
| 4,632,110 | 12/1986 | Sanagi . |
| 4,669,471 | 6/1987 | Hayashi . |
| 4,721,116 | 1/1988 | Schintgen et al. . |
| 4,763,668 | 8/1988 | Macek et al. . |
| 4,785,825 | 11/1988 | Romaniuk et al. . |
| 4,815,460 | 3/1989 | Porat et al. . |
| 4,815,476 | 3/1989 | Clossick . |
| 4,880,015 | 11/1989 | Nierman ................................. 600/564 |
| 4,887,612 | 12/1989 | Esser et al. . |
| 4,950,273 | 8/1990 | Briggs . |
| 4,953,559 | 9/1990 | Salerno . |
| 5,133,727 | 7/1992 | Bales et al. . |
| 5,152,778 | 10/1992 | Bales, Jr. et al. . |
| 5,171,256 | 12/1992 | Smith et al. . |
| 5,241,968 | 9/1993 | Slater . |
| 5,507,296 | 4/1996 | Bales et al. ............................ 600/564 |

*Primary Examiner*—Samuel Gilbert
*Attorney, Agent, or Firm*—Finnegan, Henderson, Farabow, Garrett & Dunner, L.L.P.

[57] ABSTRACT

A biological forceps device for the taking of tissue samples from a body, comprising a flexible main coil attached at its distal end to a pair of homologous cast jaws. The jaws have radially arranged teeth on their distalmost end. The jaws are opened and closed by attachment to a pair of pull wires which extend through the main coil, into a handle at its proximal end. the handle has a spool which slides about a central shaft attached to the main coil. The spool is attached to the pull wires, so that movement of the spool with respect to the central shaft, effectuates a force on the proximal ends of the levered jaws, to open and close them, appropriately.

32 Claims, 3 Drawing Sheets

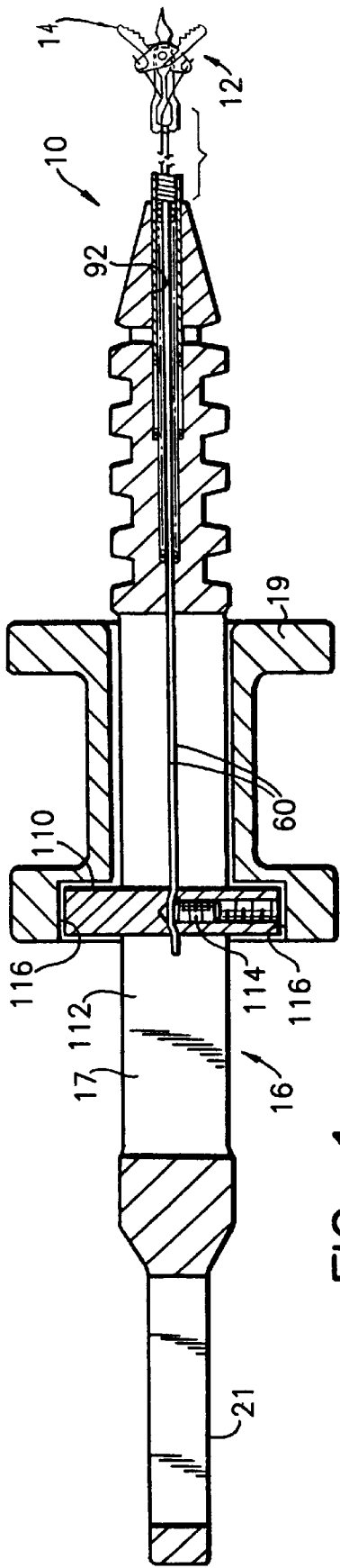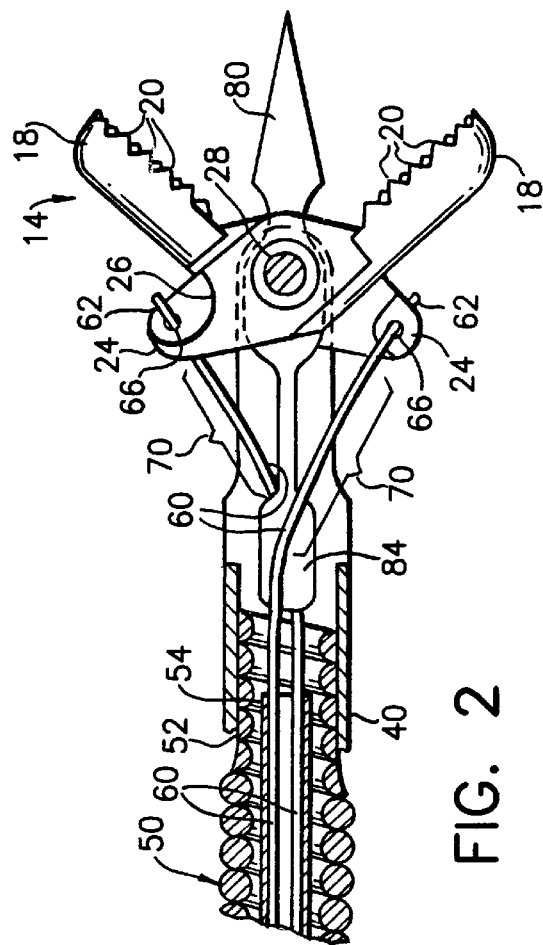

RADIAL JAW BIOPSY FORCEPS

This is a continuation division of application Ser. No. 08/458,215, filed Jun. 2, 1995, now U.S. Pat. No. 5,666,965 which is a continuation of Ser. No. 07/837,046 filed Feb. 18, 1992, now U.S. Pat. No. 5,507,296, which is a continuation of Ser. No. 07/521,766 filed May. 10, 1990 now U.S. Pat. No. 5,133,727.

BACKGROUND OF THE INVENTION

This invention relates to biopsy forceps and more particularly to unique handler actuation wire and homologous jaw construction for those forceps.

A number of different types of biopsy forceps are in common use, typically in conjunction with endoscopic assistance. Ordinarily, these devices are of complicated construction, requiring the manufacturing and machining of precise miniaturized components, which are therefore generally quite expensive.

One early example of flexible forceps is shown in U.S. Pat. No. 3,895,636 (1975) to Schmidt, wherein a pair of cup shaped jaws having an annular rim mate with a hub and a sharpened trocar. The jaws in this embodiment are of a nature which requires machining for the edge, each jaw being different from the other jaw.

U.S. Pat. No. 4,887,612 to Esser et al, shows a similar biopsy forceps which utilizes a cam linkage to effectuate the cup shaped jaws toward and away from one another. The jaws shown in this patent are made from stainless steel and likewise, require expensive machining.

U.S. Pat. No. 4,763,668 to Macek et al, shows a biopsy forceps whose cup shaped forceps are driven by a linkage arrangement. Each pivot point in the linkage establishes a new place for stress, wear and breakage. This is similar to the linkage assembly shown in U.S. Pat. No. 4,721,116 to Schintgen et al. A needle between the forceps shown in this patent, is retractable as the forceps close.

U.S. Pat. No. 3,921,640 to Freeborn, shows a surgical instrument manufactured from a single piece of molded plastic. The instrument may have any of various forms of jaws including an arrangement of teeth for holding towels or surgical dressing.

U.S. Pat. No. 4,200,111 shows a pair of spring biased jaws which are slidably disposed within the end of a trocar. The jaws are moved inwardly and outwardly from the trocar by movement from a twisted wire.

U.S. Pat. No. 4,669,471 to Hayashi, shows a biopsy forceps device having a pair of cups attached by a pivot pin, with several linkages between the cups and the operating wire, which are likewise, connected by pivot pins, the pins being welded or fused to their components by the use of laser welding.

U.S. Pat. No. 4,815,460 to Porat et al, shows a medical device for gripping, having a pair of jaws which are identical to one another. The jaws have an array of teeth disposed completely thereacross. The teeth are divided longitudinally across each jaw and are out of phase from one another by a half a pitch. The instrument is utilized for gripping purposes. A further device is shown in U.S. Pat. No. 825,829 to Heath. This appliance utilizes two different sets of engaging jaws to accomplish its cutting purpose.

It is an object of the present invention to provide a forcep device which overcomes the disadvantages of the prior art.

It is a further object of the present invention to provide a cutting device having a pair of jaws, wherein each jaw may be a duplicate of its opposing jaw.

It is yet a further object of the present invention to provide a cutting device which is self-aligning which permits greater tolerance in the dimensions of the components in their manufacture.

SUMMARY OF THE INVENTION

The present invention comprises an improvement in biopsy forceps wherein a pair of jaws are formed from a casting. Each jaw of the pair of jaws of the biopsy forceps may be a duplicate of the other jaw. Each jaw is somewhat hemispherically shaped having an elongated portion which extends proximally into a cutter tang. Each cutter jaw has a generally U-shaped distalmost end on which is defined a plurality of radially disposed teeth. The teeth on one side of the longitudinal centerline of the jaw are displaced by one-half pitch from the corresponding teeth on the other side of the longitudinal centerline on that jaw. The displacement by one-half pitch of the teeth on one side of the jaw relative to those corresponding teeth on the other longitudinal side of the jaw permits the same casting to be used for both the upper and lower jaws. The radially disposed array of teeth on each of the jaws permits a self-aligning feature therewith, thus compensating for the slightly looser tolerances found in the casting manufacturing technique.

Each jaw extends proximally and terminates in a tang, as aforementioned. Each tang is arranged so as to receive a joggled pull wire therethrough. Each jaw is mated with one another about a clevis pin which is cast unitarily with a clevis. The clevis extends into a housing which is crimped to a main coil, the proximal end of which extends into a handle having means for articulating the jaws. Each joggled pullwire from the tang on the proximal end of each jaw flexibly extends through the main coil and into the hub of the handle at the proximal end of the forceps assembly.

The handle comprises a central shaft about which a displaceable spool is disposed. The central shaft has a longitudinally directed stepped diameter bore extending therein on its distal end, and a thumb ring on its proximalmost end. The proximal end of the coil extends into the bore on the proximal end of the central shaft. The bore in the central shaft of the handle has a stepped configuration. The distal end of the bore having a slightly larger diameter than the second or intermediate bore, or the third or proximal end of the bore in the central shaft. A locking coil is arranged to mate within the stepped large outer diameter (distal end) of the central shaft. The locking coil has an inner diameter which is slightly smaller than the outer diameter of the main coil extending from the cutter jaw assembly to the handle. The main coil is screwed into the locking coil disposed within the central shaft. A sheath which acts as a strain relief, is disposed distally of the locking coil about the main coil within the central shaft. The sheath holds the locking coil within the first stepped bore in the central shaft. The strain relief is bonded to the bore of the central shaft. The proximalmost end of the joggled pull wires extend through the proximal end of the main coil and into a thin anti-kink tube in the narrowest third stepped bore in the central shaft. The cross pin fits through a slot at the midpoint of the central shaft. The slot is in communication with the third bore therein. A cross pin mates with the slot across the central shaft. The proximalmost end of the joggled pull wires are locked into an opening in the cross pin. The ends of the cross pin mate with slots in the spool so as to facilitate corresponding motion in the joggled pull wires.

Proximal movement of the spool with respect to the central shaft effectuates a pull on the joggled pull wires so as to create a pivotable motion of the tangs on the proximal end of the cutters, to cause the cutter jaws to engage to one another.

Movement of the spool distally with respect to the central shaft effectuates a compression on the pull wire thus causing arcuate movement of the tangs on the proximal end of each jaw to force a pivoting motion about the clevis pin thus opening the respective jaws.

BRIEF DESCRIPTION OF THE DRAWINGS

The objects and advantages of the present invention will become more apparent when viewed in conjunction with the following drawings, in which:

FIG. 1 is a side elevational view in section, of a biopsy forceps assembly;

FIG. 2 is a side elevational view of the distalmost end of a biopsy forceps assembly with a needle, with its cutter jaws being opened;

DETAILED DESCRIPTION OF THE PREFERRED EMBODIMENT

Figure 3:
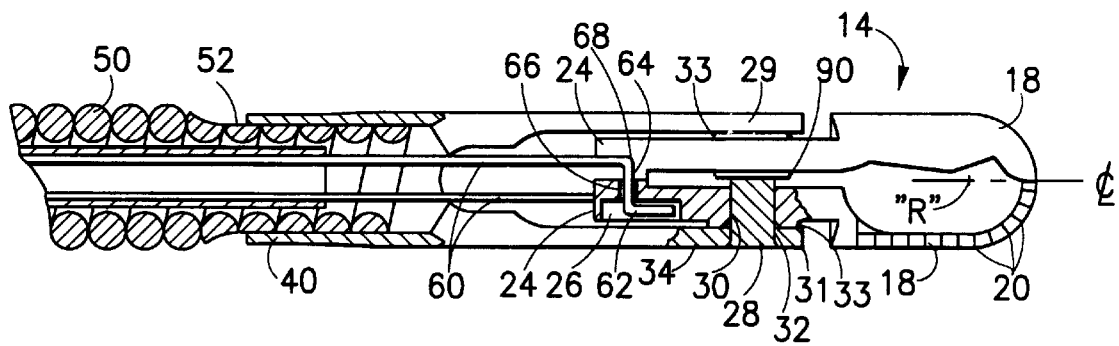
FIG. 3 is a plan view, partly in section, of the distal end of a biopsy forceps without a needle.
Figure 4:
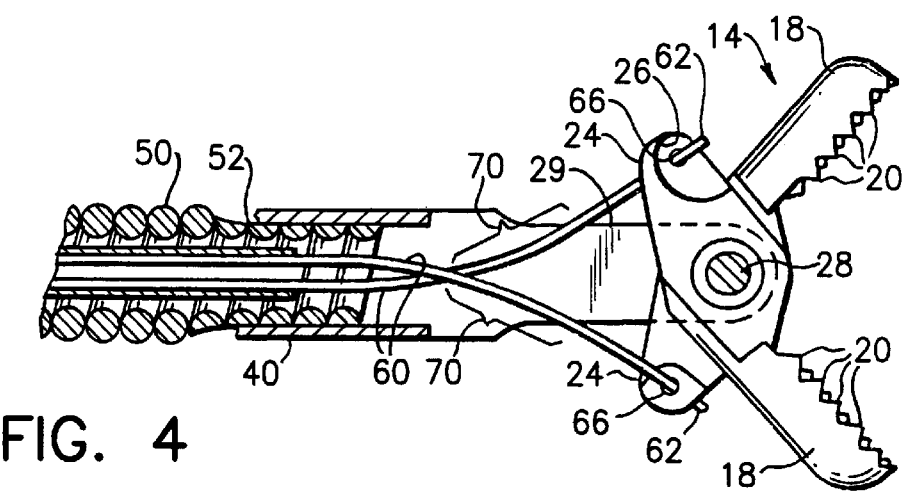
FIG. 4 is a side elevational view partly in section of the biopsy forceps shown in FIG. 3 with its jaws opened.
Figure 5:
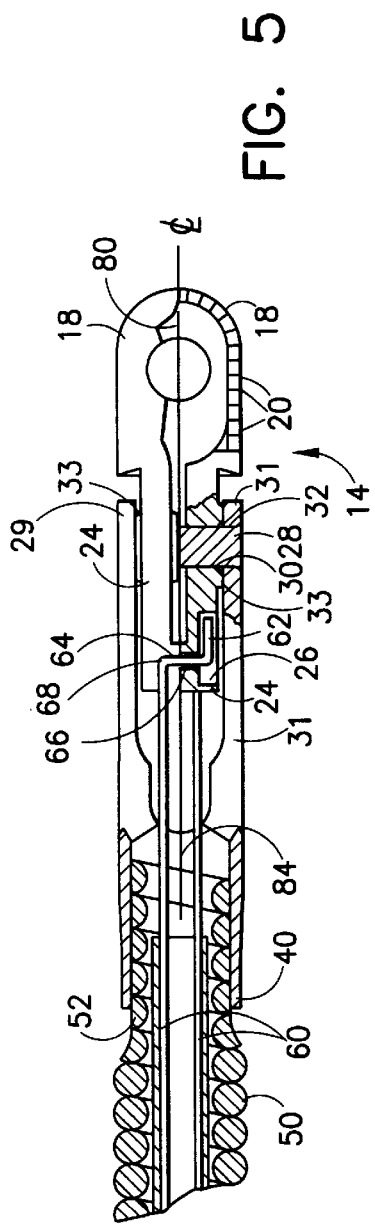
FIG. 5 is a plan view, partly in section, of the distal end of a biopsy forceps assembly, with a needle.

Referring now to the drawings in detail and particularly to FIG. 1, there is shown a biopsy forceps assembly 10, having a distal end 12, comprising a jaw assembly 14, and a proximal end 16 comprising a handle 17, spool 19 and thumb ring 21 for manipulation of the assembly. The jaw assembly 14 comprises a pair of jaws 18, each of which is a duplicate of the other. Each jaw 18 as may be seen in FIGS. 2 and 3, is a generally elongated somewhat hemispherically shaped structure having a distalmost end and a proximalmost end. Each jaw 18 has on its distalmost end, an array of teeth 20 generally radially directed about a point "R", as exemplified in FIG. 3. Each jaw 18 has a generally longitudinal centerline as may be seen in FIGS. 3 and 5. The teeth 20 on one side of the longitudinal centerline of each jaw 18 being displaced by one half pitch from the corresponding teeth 20 on the other side of the longitudinal centerline on that jaw 18. The displacement by one half pitch by the teeth on one side of the jaw 18 is relative to those corresponding teeth 20 on the other longitudinal side of the jaw 18 permits the same casting to be used for both the upper and lower jaws of the jaw assembly 14. The radial arrangement of the teeth 20 as best seen in FIGS. 3 and 5 require each jaw 18 when they close onto one another to automatically mate and effectuate proper alignment therebetween. The self-alignment permits each jaw 18 to be manufactured by an investment casting technique which is inherantly less expensive than the typical prior art jaws which are machined and which distalmost teeth are either non-existant or they are transverse to the longitudinal centerline the jaws, which jaws inherantly fail to have any positive cutting edge at their distalmost ends. The casting of each jaw 18 also permits a looser tolerance therebetween which is characteristic of the casting manufacturing technique without any loss in effectiveness of those jaws.

Each jaw 18 has a proximalmost end which comprises a tang 24. Each tang 24 has a generally semicircular recess position 26 on its outer side thereof. The recessed portion 26 may be seen most clearly in FIGS. 3 and 5, and then a side view in FIGS. 2, 4 and 6. A bore 30 extends transversely through the midpoint between the distal and proximalmost ends of each jaw 18. Each jaw 18 is mated with one another and so as to each be levered about a clevis pin 28 which extends through the bore 30 on each respective jaw 18. Each jaw 18 has an annular boss 33 disposed about the outer face of its bore 30, as shown in FIGS. 3 and 5. The boss 33 acts as a bearing surface to reduce the typical friction found on prior art forceps. The clevis pin 28 is received in a hole 32 in clevis 34 as shown in FIGS. 3 and 5. The clevis 34 extends proximally, as shown in FIGS. 2–6, into a hub 40. The clevis 34, the housing 40 and clevis pin 28 are made from a common casting. The clevis pin 28 unitarily extending from one of the sidearms 29 Of the clevis 34.

A main tubular coil 50 shown in FIG. 2 at its distal end thereof, has a portion of it periphery ground flat, as at 52. The flattened distal periphery of the main coil 50 permits a more solid anchoring between the inside of the hub 40 and the distal end of the main coil 50 when the two are crimped together,. obviating the need for adhesives, soldering or welding.

Figure 7:
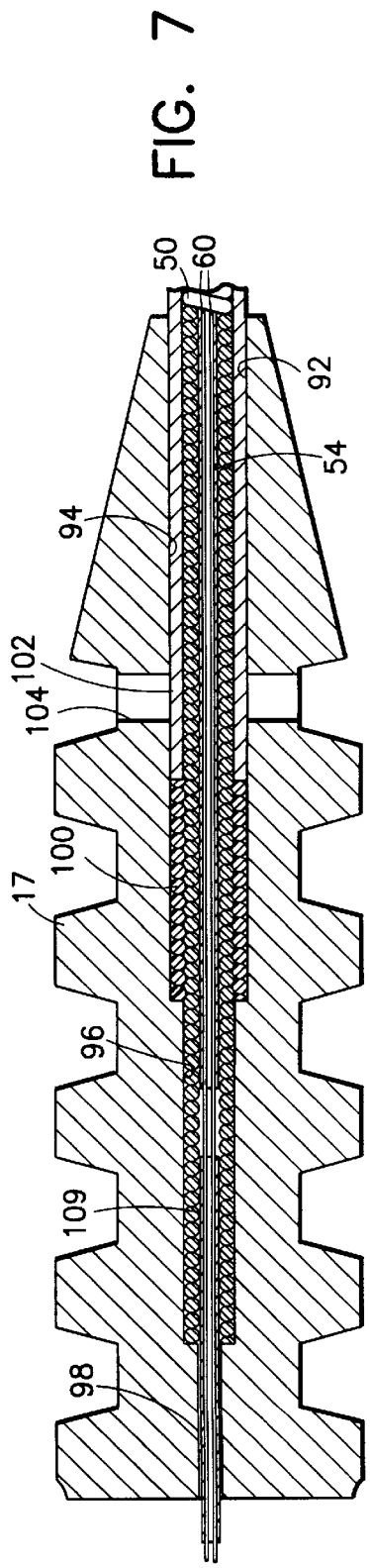
FIG. 7 is a side elevational view in section, showing part of the handle at the proximalmost end of a biopsy forceps assembly.

An FEP sheath 54 extends from the distal end of the main coil 50 therethrough into the central shaft 56 of the handle 17 as shown in FIGS. 2 and 7. This sheath 54 acts as a bearing between a pair of pull wires 60 and the lumen of the main coil 50.

The distalmost end of each pull wire 60 has a Z-bend therein. the Z-bend of each pull wire 60 has a first portion 62 which is rotatably disposed in the recess 26 in the tang 24 of each cutter jaw 18. The Z-bend has a second portion 64 which extends through a bore 66 in the proximalmost end of the tang 24, as best shown in FIGS. 3 and 5. A ninety degree bend 68 between the second portion 64 and the main pull wire 60 eliminates the pinching common to prior art loop design wires. Each pull wire 60 has a reflex curve 70 as shown in FIG. 2 as well as in FIGS. 6 and 7, extending between their distalmost ends and the distalmost end of the main coil 50. The reflex curve 70 helps to open the cutter jaws 18 when the spool 19 on the handle 17 is displaced distally thereto.

Figure 6:
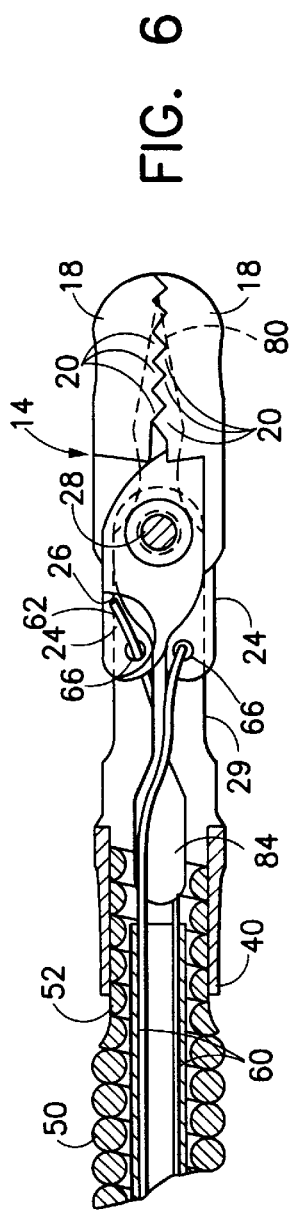
FIG. 6 is a side elevational view partly in section, of the biopsy forceps shown in FIG. 5.

FIGS. 2, 5 and 6 shows the distal end of the biopsy forceps assembly 10 with a flat needle 80 disposed between the two cutter jaws 18. The needle 80 has a pointed distalmost end 82 that terminates just within the cutter jaws 18 when closed, and has tail 84 comprising its proximalmost end which extends within the distalmost end of the main coil 50. The needle 80 has a central opening through which the clevis pin 28 may extend as shown in FIGS. 3 and 5. The needle 80 is flat, and as such may be disposed between the two tangs 24 of each cutter jaw 18 as shown in FIG. 5. In cutter jaw assembly 14 without the needle therein, a washer 90 is disposed between the two cutter jaws 18 on the clevis pin 28.

The proximal end of the main coil 50 and the proximal end of the pull wires 60 extend into handle 17 at the proximal end 16 of the biopsy forceps assembly 10. The handle 17 comprises a central shaft about which a displaceable spool 19 is disposed. The central shaft has a longitudinally directed stepped diameter bore 92 extending therein, as shown in FIGS. 1 and 7. The proximal end of the main coil 50 extends into the bore 92 on the proximal end of the central shaft. The bore 92 extending into the central shaft has a three stepped configuration. The bore 92 on the distalmost end of the central shaft has a large first diameter 94 as shown in FIG. 7 which steps to a smaller second diameter 96 which subsequently steps down to a smaller yet third diameter bore 98. A locking coil 100 is disposed against the first largest diameter bore 94 in the central shaft. The main coil 50 has an outer diameter slightly larger than the inner diameter of the locking coil 100 and is threadedly received therethrough. The main coil 50 thus extends to and abuts the handle 17 adjacent the second stepped bore 96 of the bore 92 in the central shaft. The pull wires 60 disposed through the inner lumen of the main coil extend therethrough and into the smallest portion 98 of the bore 92 in the central shaft. A strain relief sheath 102 is disposed distally to the locking coil about the main coil 50 within the largest bore 94 in the central shaft. The strain relief sheath 102 extends slightly distally of the distalmost end of the central shaft, and is bonded to the inner walls of the largest bore 94 by a solvent which is directed thereto through a hole 104, as shown in FIG. 7. The strain relief sheath 102 limits twist and movement of the main coil 50 with the bore 94 while preventing a sharp bend of the coil 50 at the distal end of the handle 17. The proximalmost end of the pull wires 60 extend through the proximal end of the main coil 50 as aforementioned and through and anti-kinking tube 109, and are locked into a cross pin 110, as shown in FIG. 1, which cross pin 110 mates with a slot 112 disposed across the central shaft of the handle 17. The slot 112 is in communication with the axial bore 92 in the central shaft. The proximalmost end of the pull wires 60 are locked into the cross pin 110 by a set screw 114 as shown in FIG. 1. The ends of the cross pins 110 mate with a slot 116 in the spool so as to lock the cross pin 110 therewith. Movement of the spool 19 which is disposed about the central shaft thereby effectuates movement of the puller wires 60 disposed within the main coil 50, the distal ends of which are attached to the tangs 24 on the cutter jaws 18 as shown in FIGS. 1 and 2.

Thus there has been shown a biopsy forceps assembly which can be made in a very cost effective manner for an improved biopsy sample. The cutter jaws and clevis support of the biopsy forceps each being made of a cast material permitting a far less expensive manufacture because of its simplicity permitting one jaw design and its self-aligning radially directed distal jaw teeth effectuating its cutting effectiveness as well as its ease of assembly. The pull wire arrangement with each particular jaw eliminates the prior art multiple linkages which have frictional problems and potential for breakage therewith. The spool design for the grasping of the pull wires in regard to the handle therewithin facilitates a one-handed operation thus permitting the physician use of his other hand for other purposes.

We claim:

1. A biopsy forceps device having a proximal end and a distal end, the device comprising:
   an end effector assembly at the distal end of the device, wherein the end effector assembly includes a first jaw and a second jaw, the first jaw being pivotally disposed about a pivotal axis and with respect to the second jaw;
   an actuator at the proximal end of the device; and
   a hollow portion connecting the end effector assembly and the actuator, wherein the actuator operates to pivot the first jaw about the pivotal axis and move the first jaw into contact with the second jaw, wherein each of the first and second jaws includes a generally U-shaped configuration defining a center point and having a distalmost end, and wherein an edge of the distalmost end of each of the jaws includes teeth radially disposed about the center point.

2. The device according to claim 1, wherein the second jaw is pivotally disposed about the pivotal axis and with respect to the first jaw so that the jaws mate upon pivotal movement.

3. The device according to claim 2, further comprising a clevis pin, wherein the pivotal axis is defined by the clevis pin.

4. The device according to claim 1, wherein the teeth have a substantially triangular shape.

5. The device according to claim 4, wherein the teeth of the first and second jaws mate.

6. The device according to claim 5, wherein the teeth of the first jaw are displaced by one half pitch from the teeth of the second jaw.

7. The device according to claim 1, wherein the first and second jaws have a generally elongated hemispherical shape.

8. The device according to claim 1, wherein the first jaw has a tang defining a first bore.

9. The device according to claim 8, further comprising a first pull wire positioned within the hollow portion, the first pull wire connecting the first jaw to the actuator and engaging the first bore, wherein a distal end of the first pull wire passes through and beyond the first bore and terminates without forming a loop.

10. The device according to claim 9, further comprising a second pull wire positioned within the hollow portion and connecting the second jaw to the actuator.

11. The device according to claim 10, wherein the second jaw has a tang defining a second bore and the second pull wire engages the second bore, a distal end of the second pull wire passing through and beyond the second bore and terminating without forming a loop, the actuator operating to pivot the second jaw about the pivotal axis.

12. The device according to claim 11, wherein the distal end of the second pull wire includes a main portion which extends in the direction of the actuator, a first portion which passes through the second bore at an angle to the main portion, and a second portion on the opposite side of the second bore relative to the main portion, the second portion of the second pull wire maintaining the second pull wire on the tang, the second pull wire terminating on the second portion.

13. The device according to claim 10, wherein the actuator includes a handle being coupled to the first and second pull wires.

14. The device according to claim 13, wherein the handle includes a central shaft and a spool slidably disposed around the central shaft, the spool engaging the first and second pull wires, the spool operable to move the first and second pull wires relative to the central shaft.

15. The device according to claim 10, wherein the first and second pull wires are positioned within the hollow portion for a substantial length of the hollow portion.

16. The device according to claim 9, wherein the distal end of the first pull wire includes a main portion which extends in the direction of the actuator, a first portion which passes through the first bore at an angle to the main portion, and a second portion on the opposite side of the first bore relative to the main portion, the second portion of the first pull wire maintaining the first pull wire on the tang, the first pull wire terminating on the second portion.

17. The device according to claim 16, wherein the first pull wire is bent between the main portion and the first portion and between the first portion and the second portion.

18. The device according to claim 17, wherein the first portion of the first pull wire which passes through the bore is rotatable relative to the surface of the bore.

19. The device according to claim 1, wherein the hollow portion is a coil.

20. The device according to claim 1, further comprising a needle disposed between the first and second jaws.

21. An end effector assembly for use in a biopsy forceps device including an actuator at a proximal end of the device and a hollow portion connecting the actuator to the end effector assembly, the end effector assembly comprising:

a first jaw; and a second jaw for mating with the first jaw, wherein the first jaw is pivotally disposed with respect to the second jaw about a pivotal axis, and each of the first and second jaws includes a generally U-shaped configuration defining a center point and having a distalmost end, and wherein an edge of the distalmost end of each of the jaws includes teeth radially disposed about the center point.

22. The assembly according to claim 21, wherein the second jaw is pivotally disposed about the pivotal axis and with respect to the first jaw so that the jaws mate upon pivotal movement.

23. The assembly according to claim 22, further comprising a clevis pin, wherein the pivotal axis is defined by the clevis pin.

24. The device according to claim 22, wherein the second pull wire is bent between the main portion and the first portion and between the first portion and the second portion.

25. The device according to claim 24, wherein the first portion of the second pull wire which passes through the second bore is rotatable relative to surface of the bore.

26. The assembly according to claim 21, wherein the teeth have a substantially triangular shape.

27. The assembly according to claim 26, wherein the teeth of the first and second jaws mate.

28. The assembly according to claim 27, wherein the teeth of the first jaw are displaced by one half pitch from the teeth of the second jaw.

29. The assembly according to claim 21, wherein the first and second jaws have a generally elongated hemispherical shape.

30. The assembly according to claim 21, wherein the first jaw has a tang defining a first bore for receiving a first pull wire.

31. The assembly according to claim 21, wherein the second jaw has a tang defining a second first bore for receiving a second pull wire.

32. The assembly according to claim 21, further comprising a needle disposed between the first and second jaws.

* * * * *